(12) United States Patent
McKinley et al.

(10) Patent No.: US 8,278,491 B2
(45) Date of Patent: Oct. 2, 2012

(54) PROCESS FOR THE CO-PRODUCTION OF FATTY ALCOHOLS SHOWING DIFFERENT CARBON CHAIN LENGTHS

(75) Inventors: Donald Hugh McKinley, London (GB); Richard John Hensman, London (GB); Andrew George Hiles, London (GB); Rikard Umberto Andersson, London (GB)

(73) Assignee: Davy Process Technology Limited, London (GB)

( * ) Notice: Subject to any disclaimer, the term of this patent is extended or adjusted under 35 U.S.C. 154(b) by 250 days.

(21) Appl. No.: 12/681,575

(22) PCT Filed: Oct. 3, 2008

(86) PCT No.: PCT/GB2008/050905
§ 371 (c)(1),
(2), (4) Date: Jul. 2, 2010

(87) PCT Pub. No.: WO2009/044210
PCT Pub. Date: Apr. 9, 2009

(65) Prior Publication Data
US 2010/0286454 A1    Nov. 11, 2010

(30) Foreign Application Priority Data
Oct. 3, 2007   (GB) .................................. 0719251.1

(51) Int. Cl.
*C07C 29/149* (2006.01)
*C07C 27/04* (2006.01)

(52) U.S. Cl. ........................................................ 568/885
(58) Field of Classification Search .................... 568/885
See application file for complete search history.

(56) References Cited

U.S. PATENT DOCUMENTS 6,184,424 B1 * 2/2001 Bueschken et al. ........... 568/882
2005/0222469 A1 * 10/2005 Namba et al. ................. 568/885

FOREIGN PATENT DOCUMENTS

| DE | 4321837 A1 | 1/1995 |
| GB | 2116552 | 9/1983 |
| WO | 8203854 | 11/1982 |
| WO | 9008127 | 7/1990 |
| WO | 9614280 A | 5/1996 |
| WO | 9614280 A1 | 5/1996 |

OTHER PUBLICATIONS

International Search Report for PCT/GB2008/050905, dated Feb. 20, 2009, 2 pages.
International Preliminary Report on Patentability & Written Opinion for PCT/GB2008/050905, dated Apr. 7, 2010, 7 pages.

* cited by examiner

*Primary Examiner* — Brian J Davis
(74) *Attorney, Agent, or Firm* — Armstrong Teasdale LLP

(57) ABSTRACT

A process for the co-production of a stream of a fatty alcohol having first carbon chain lengths and a stream of a fatty alcohol having second carbon chain lengths, said second carbon chain lengths being longer than said first carbon chain lengths.

13 Claims, 2 Drawing Sheets

PROCESS FOR THE CO-PRODUCTION OF FATTY ALCOHOLS SHOWING DIFFERENT CARBON CHAIN LENGTHS

The present invention relates to a process for the production of fatty alcohols. More particularly, it relates to a process for the co-production of a stream of a fatty alcohol having first carbon chain lengths and a stream of a fatty alcohol having second carbon chain lengths wherein the second carbon chain lengths are longer than the first carbon chain lengths. In one arrangement, the present invention relates to the co-production of a stream of a $C_8/C_{10}$ fatty alcohol and a stream of a $C_{12}/C_{14}$ fatty alcohol. In a second preferred arrangement, the present invention relates to the co-production of a $C_{12}/C_{14}$ fatty alcohol and a stream of a $C_{16}/C_{18}$ fatty alcohol.

Fatty alcohols having more than 12 carbon atoms, which are sometimes known as higher alcohols, are monohydric aliphatic alcohols. These may be derived either from natural sources or they may be synthesised such as from petroleum feedstocks. Since alcohols having from about 11 to about 20 carbon atoms are often used in the production of synthetic detergents, they may be referred to as detergent alcohols or detergent range alcohols.

Detergent range alcohols are typically produced by hydrogenation of lower alkyl, such as methyl or ethyl, esters of the corresponding carboxylic acids. These esters can be produced by any suitable means but may be produced by transesterification of natural triglycerides or by esterification of the carboxylic acids obtained by hydrolysis of the triglycerides. Examples of triglycerides which may be used as raw materials include natural oils, such as coconut oil, rape seed oil and palm oils and animal fats such as lard, tallow and fish oil. As these natural raw materials usually contain mixtures of triglycerides, the alcohol products obtained from the hydrogenation are mixtures of n-alcohols of differing molecular weight. Whilst for some end-uses, separation of the alcohol mixtures is not required, for many it is desirable that the alcohols present in the product stream has as narrow a range of carbon chain lengths as possible. In general, the desired product stream will comprise alcohols having chain lengths differing by only three carbon atoms. Examples of suitable alcohol mixtures are those having from $C_{12}$ to $C_{14}$ fatty alcohols or from $C_{16}$ to $C_{18}$ fatty alcohols.

The esters usually used as raw materials for the production of detergent range alcohols are the methyl esters. However, a problem arises in refining the product alcohol mixtures because the boiling point of one or more of the methyl esters present in the starting ester mixture will usually be close to that of the desired product alcohols. Hence it is difficult to separate any unconverted methyl esters from the product alcohol mixture by distillation.

In addition to the problems associated with the separation of products from each other and from unreacted starting materials and by-products, problems are also encountered where a range of chain lengths are present during the hydrogenation process. In particular, the longer chain alcohols, i.e. those having 16 or more carbon atoms, tend to be retained in the hydrogenation reaction zone for a significant period of time. Without wishing to be bound by any theory, it is believed that the alcohols are absorbed by the catalyst. Whilst this retention in the reaction zone will generally tend to result in higher ester conversion, it will generally also be accompanied by higher production of undesirable by-products such as alkanes.

In contrast, the shorter chain alcohols, i.e. those having less than 16 carbon atoms tend to pass through the reaction zone more quickly. Again without wishing to be bound by any theory, it is believed that these shorter alcohols are absorbed less by the catalyst. Whilst this does have the benefit of reducing the production of undesirable by-product alkanes, it also has the effect of lowering the rate of conversion for these lower chain length esters to the desired alcohols.

It will therefore be understood that for a feed stream comprising a mixture of longer and shorter chain lengths, the reactor effluent will generally have a preponderance of shorter chain unreacted esters and longer chain alkanes rather than the desired mixture of shorter and longer chain fatty alcohols. Although the longer chain alkanes can be removed, the removal is difficult as they have close boiling points to the shorter chain alcohols.

Whilst it is possible to arrange conditions such that the amount of alkane production is reduced to avoid the difficult distillation, the conversion rate to the desired alcohol product will also be reduced. To mitigate the reduced conversion, it is desirable to include a wax ester recycle. However, in view of the low conversion rate a substantial wax ester recycle will be required which will add substantially to the costs.

It will therefore be understood that effective processing of a wide range of chain lengths in the feed simultaneously in a single reaction step is very difficult and in some cases impossible. Where the reaction is possible it is generally found to be uneconomic.

In order to overcome the problems detailed above, three processes have been suggested to date. The first is to feed separated acids to a single plant sequentially in what is known as a "campaign operation". The benefit of this mode of operation is that the conditions for processing each acid can be optimised. However, this mode of operation has the disadvantage of requiring complex and expensive separation steps for the acids. In addition, the separated acids must be subjected to separate esterification processes which adds to the costs. A further disadvantage of this mode of operation is the reduced capacity for the hydrogenation reactor due to the sequential nature of the process.

The second proposed process is to feed separated esters to a single plant sequentially in a "campaign operation". As with the first option, this suffers from the drawback of the need to separate the esters and the reduced capacity of the hydrogenation plant.

The third proposed process is to use two or more parallel plants. Whilst this process overcomes the capacity limitations of the campaign operations of the first and second processes, this process also requires the separation steps to be carried out and requires the capital and operating costs for two plants.

It will therefore be understood that each of the proposed processes is uneconomical and there is therefore a need for a process which enables the problems detailed above that are associated with treating a feedstock comprising lower alkyl esters of a mixture of differing chain length carboxylic acids to be overcome. It is also desirable to provide a process which is economical to operate.

A process has now been established that enables the desired cuts of $C_{12}/C_{14}$ and $C_{16}/C_{18}$ alcohols to be formed in an efficient and economical manner. The process may also be operated to allow for the co-production of a stream of a fatty alcohol having first carbon chain lengths, which may be $C_8/C_{10}$, and a stream of a fatty alcohol having second carbon chain lengths which may be $C_{12}/C_{14}$ or $C_{10}/C_{12}$.

For the avoidance of doubt, the terms "$C_{12}/C_{14}$" alcohols, acids or their esters mean streams comprising predominately alcohols, acids or their esters respectively having from about 12 to about 14 carbon atoms in the chain. Similarly the term "$C_{16}/C_{18}$" alcohols, acids or their esters mean streams comprising predominately alcohols, acids or their esters respectively having from about 16 to about 18 carbon atoms in the chain. These terms should therefore be construed accordingly. It will be understood that minor amounts of alcohols, acids or their corresponding esters having carbon chain lengths outside these ranges may also be present in the streams as may other impurities.

Similarly references to a stream comprising a lower alkyl ester of "$C_{12}/C_{18}$" fatty acids means a stream comprising lower alkyl esters of carboxylic acids being a mixture of chain lengths in the acid chain of from about 12 to about 18 carbon atoms. Again it will be understood that minor amounts of acids and their corresponding esters having carbon chain lengths outside these ranges may also be present in the streams as may other impurities. Other chain length cuts should be construed in a corresponding manner.

Thus according to the present invention, there is provided a process for the co-production of a stream of a fatty alcohol having first carbon chain lengths and a stream of a fatty alcohol having a second carbon chain lengths, said second carbon chain lengths being longer than said first carbon chain lengths, said process comprising the steps of:

(a) supplying a stream comprising lower alkyl esters of fatty acids having chain lengths comprising the first and second chain lengths to a first vaporisation zone and contacting said stream with an amount of hydrogen which is sufficient to vaporise the lower alkyl esters of the fatty acids having the first carbon chain lengths into the hydrogen;

(b) supplying the hydrogen and the vaporised lower alkyl esters of fatty acids having the first carbon chain lengths to a first reaction zone comprising catalyst and operating under reaction conditions to allow hydrogenation to the desired alcohol having first carbon chain lengths;

(c) recovering from the first reaction zone an alcohol product stream having first carbon chain lengths and hydrogen;

(d) separating the stream of fatty alcohol having the first carbon chain lengths from hydrogen;

(e) supplying the unvaporised lower alkyl esters of the fatty acids having second carbon chain lengths remaining from step (a) to a second vaporisation zone;

(f) contacting the unvaporised lower alkyl esters having second carbon chain lengths in the second vaporisation zone with hydrogen recovered in step (d) and an additional amount of hydrogen such that the total amount of hydrogen is sufficient to vaporise the lower alkyl esters having fatty acids of the second carbon chain lengths into the hydrogen;

(g) supplying the hydrogen and the vaporised lower alkyl esters of fatty acids having second carbon chain lengths to a second reaction zone comprising catalyst and operating under reaction conditions to allow hydrogenation to the desired alcohol having second carbon chain lengths; and (h) recovering from the second reaction zone an alcohol product stream having second carbon chain lengths and hydrogen.

In a preferred process of the present invention there is provided a process for the co-production of a stream of a $C_{12}/C_{14}$ fatty alcohol and a stream of a $C_{16}/C_{18}$ fatty alcohol comprising the steps of:

(a) supplying a stream comprising lower alkyl esters of $C_{12}/C_{18}$ fatty acids to a first vaporisation zone and contacting said stream with an amount of hydrogen which is sufficient to vaporise the lower alkyl esters of the $C_{12}/C_{14}$ fatty acids into the hydrogen;

(b) supplying the hydrogen and the vaporised lower alkyl esters of $C_{12}/C_{14}$ fatty acids to a first reaction zone comprising catalyst and operating under reaction conditions to allow hydrogenation to the desired $C_{12}$-$C_{14}$ alcohol;

(c) recovering from the first reaction zone a $C_{12}/C_{14}$ alcohol product stream and hydrogen;

(d) separating the stream of $C_{12}/C_{14}$ fatty alcohol from hydrogen;

(e) supplying the unvaporised lower alkyl esters of $C_{16}/C_{18}$ remaining from step a second vaporisation zone;

(f) contacting the unvaporised lower alkyle esters of $C_{16}/C_{18}$ in the second vaporisation zone with hydrogen recovered in step (d) and an additional amount of hydrogen such that the total amount of hydrogen is sufficient to vaporise the lower alkyl esters of the $C_{16}/C_{18}$ fatty acids into the hydrogen;

(g) supplying the hydrogen and the vaporised lower alkyl esters of $C_{16}/C_{18}$ fatty acids to a second reaction zone comprising catalyst and operating under reaction conditions to allow hydrogenation to the desired $C_{16}/C_{18}$ alcohol; and (h) recovering from the second reaction zone a $C_{16}/C_{18}$ alcohol product stream and hydrogen.

Thus in the process of the present invention there is no requirement to separate the acids or their esters. By supplying the first vaporisation zone with only sufficient hydrogen to vaporise the lower alkyl esters of $C_{12}/C_{14}$ fatty acids but not the esters of the $C_{16}/C_{18}$ fatty acids, the hydrogen serves to strip the lower alkyl esters of $C_{12}/C_{14}$ fatty acids from the esters of the $C_{16}/C_{18}$ fatty acids.

Further, since the hydrogen used in the first vaporisation zone and the first reaction zone is separated from the product stream and reused in the second vaporisation zone in combination with sufficient hydrogen to meet the requirement of hydrogen in the second vaporisation zone, the overall cycle gas requirement of the process to process both cuts is minimised. This has the benefit of reducing the capital and operating costs.

Thus the process of the present invention obviates the need for difficult and expensive separation of the $C_{12}/C_{14}$ esters or acids from the $C_{16}/C_{18}$ esters or acids, reduces the cycle gas requirement for the system which reduces the operating and equipment costs and enables the processing to the desired $C_{12}/C_{14}$ fatty alcohol and $C_{16}/C_{18}$ fatty alcohol to be carried out in the optimum manner for each stream.

The amount of hydrogen required in step (a) is sufficient to vaporise the fatty acid esters having the first carbon chain lengths. Establishing the amount of hydrogen required for any particular feed will be a matter of routine for the skilled man. In particular the amount of hydrogen supplied to the vaporiser in step (a) of the preferred embodiment of the present invention can be calculated based on the minimum hydrogen flow to just vaporise the lower alkyl esters of $C_{12}/C_{14}$ fatty acids based on the published vapour pressure for each of the components. A similar calculation can be made to establish the amount of hydrogen required in step (f).

The lower alkyl esters of the $C_{12}/C_{18}$ fatty acids which provides the feed to the process of the present invention may be produced by any suitable means.

Any suitable amount of hydrogen may be provided to the first vaporisation zone provided that it is sufficient to vaporise the lower alkyl esters of the $C_{12}/C_{14}$ fatty acids. In one arrangement, the amount of hydrogen provided may be the stoichiometric amount required for the amount of lower alkyl esters of the $C_{12}/C_{14}$ fatty acids supplied to the first vaporisation zone.

Any suitable reaction conditions may be used. In one arrangement, the temperature may be from about 150° C. to about 300° C., preferably from about 175° C. to about 250° C., more preferably about 200° C. The pressure may be from about 400 psig to about 600 psig, more preferably from about 500 psig to about 600 psig. The hydrogen recycle flow rate may be from about 300 g/hr to about 500 g/hr.

The stream leaving the first vaporisation zone will therefore be the hydrogen stream into which the lower alkyl esters of the $C_{12}/C_{14}$ fatty acids has been vaporised and thus the lower alkyl esters of the $C_{12}/C_{14}$ fatty acids will be carried forward to the first reactor with the hydrogen.

The hydrogenation conditions in the first reaction zone are selected such that the hydrogenation of the lower alkyl esters to the desired alcohols is effected in the vapour phase. In general conditions will be arranged such that the material in contact with the hydrogenation catalyst is above the dew point. Typical vapour phase hydrogenation conditions include use of temperatures of from about 150° C. to about 300° C., preferably from about 175° C. to about 250° C., more preferably about 200° C. Any suitable pressure may be used. Suitable pressures include those in the range of from about 5 bar to about 100 bar. 400 psig to about 600 psig, more preferably from about 500 psig to about 600 psig. The hydrogen recycle flow rate may be from about 300 g/hr to about 500 g/hr.

Any suitable hydrogenation catalyst may be used provided that it will catalyse the vapour phase hydrogenation of the ester to the desired alcohol. In general a heterogeneous catalyst will be used. Suitable hydrogenation catalysts include known hydrogenation catalysts such as reduced copper oxide-zinc oxide, copper chromite and promoted copper chromite catalysts. Details of the reduced copper oxide-zinc oxide catalysts can be found in GB 2116552 and WO 82/03854 which are incorporated herein by reference.

The hydrogen stream, having had been separated from the desired alcohols, any unreacted esters and any by-products is then supplied to the second vaporisation zone. The hydrogen is combined with the additional hydrogen which is required to vaporise the lower alkyl esters of the $C_{16}/C_{18}$ carboxylic acids. The stream of hydrogen from the first reaction zone may be combined with the additional hydrogen in the second vaporisation zone or they may be combined prior to the second vaporisation zone such that a single hydrogen stream is supplied to the second vaporisation zone.

Any suitable amount of hydrogen may be provided to the second vaporisation zone provided that it is sufficient to vaporise the lower alkyl esters of the $C_{16}/C_{18}$ fatty acids. In one arrangement, the amount of hydrogen provided may be the stoichiometric amount required for the amount of lower alkyl esters of the $C_{16}/C_{18}$ fatty acids supplied to the second vaporisation zone.

The stream leaving the second vaporiser will therefore be the hydrogen stream into which the lower alkyl esters of the $C_{16}/C_{18}$ fatty acids have been vaporised and thus the lower alkyl esters of the $C_{16}/C_{18}$ fatty acids will be carried forward to the second reactor with the hydrogen.

The hydrogenation conditions in the second reaction zone are selected such that the hydrogenation of the lower alkyl esters to the desired alcohols is effected in the vapour phase. In general conditions will be arranged such that the material in contact with the hydrogenation catalyst is above the dew point. Typical vapour phase hydrogenation conditions include those detailed above.

The catalyst used in the second reaction zone may be the same or different to that used in the first reaction zone. In general a heterogeneous catalyst will be used. Suitable hydrogenation catalysts include known hydrogenation catalysts such as reduced copper oxide-zinc oxide, copper chromite and promoted copper chromite catalysts. Details of the reduced copper oxide-zinc oxide catalysts can be found in GB 2116552 and WO 82/03854 which are incorporated herein by reference.

The desired product $C_{16}/C_{18}$ alcohol can then be recovered from the second reaction zone. The hydrogen may then be recycled for use in the process. Make-up hydrogen may be added as required to maintain the total amount of hydrogen in the system and, if appropriate, a purge may be taken to prevent the build-up of undesirable material in the system.

The first and second vaporisation zones may be separate zones in the same vaporiser or may be separate vaporisers. Similarly, the first and second reaction zones may be separate zones in the same reactor or may be separate reactors.

BRIEF DESCRIPTION OF THE DRAWINGS

The present invention will now be described by way of example with reference to the accompanying drawings, in which.

It will be understood that the drawings are diagrammatic and that further items of equipment such as reflux drums, pumps, vacuum pumps, temperature sensors, pressure sensors, pressure relief valves, control valves, flow controllers, level controllers, holding tanks, storage tanks and the like may be required in a commercial plant. The provision of such ancillary items of equipment forms no part of the present invention and is in accordance with conventional chemical engineering practice.

Figure 1:
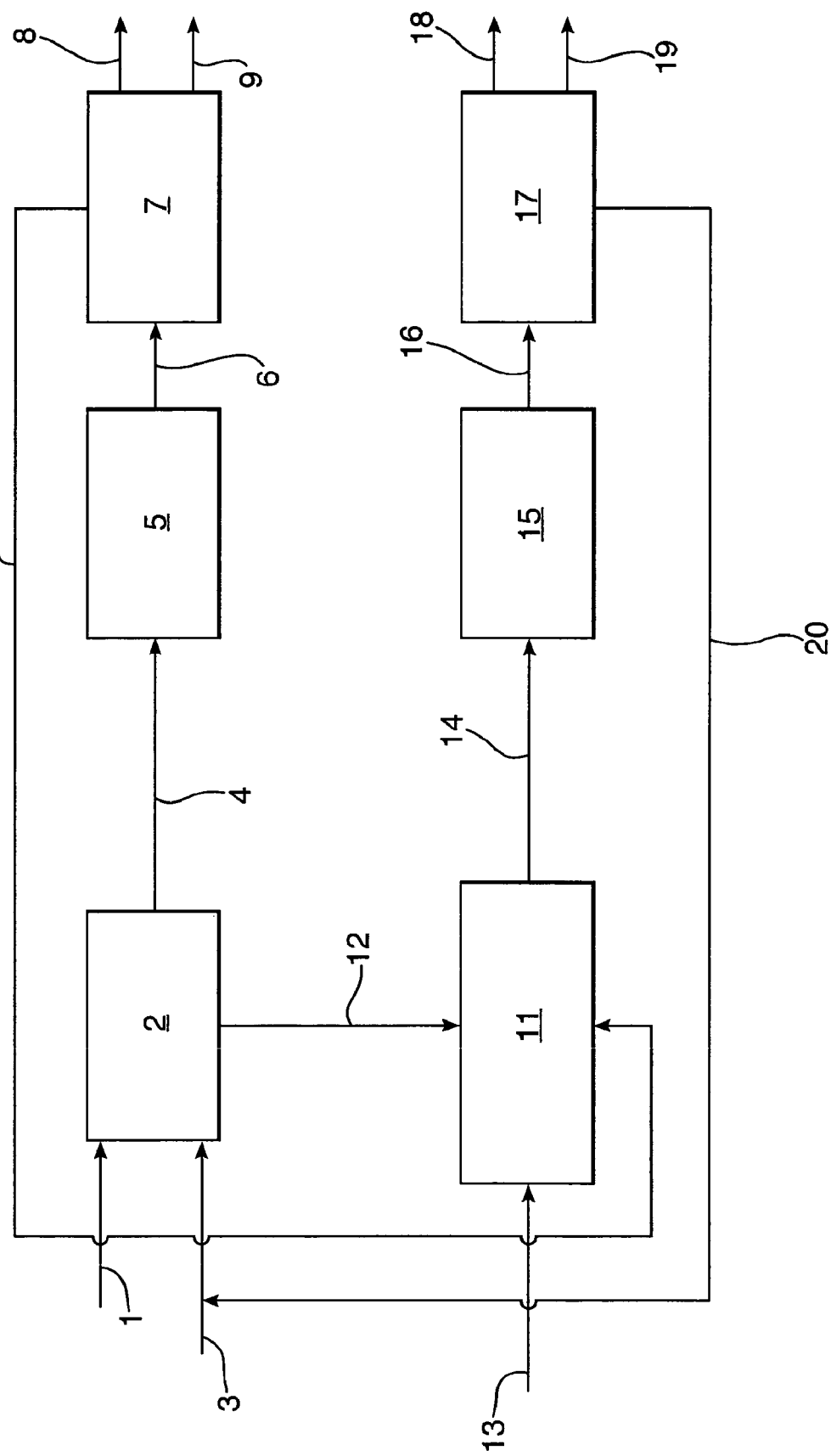
FIG. 1 is a simplified schematic representation of the process of the present invention.

As illustrated in FIG. 1, a feed stream is fed in line 1 to a first vaporisation zone 2. The feed stream comprises a lower alkyl ester, preferably a lower methyl ester, of $C_{12}/C_{14}/C_{16}/C_{18}$ carboxylic acids. The esters may have been formed by any suitable means. Examples of a suitable esterification process is described in EP0454719 which is incorporated herein by reference. The first vaporisation zone 2 is provided with hydrogen in line 3. The amount of hydrogen provided will be sufficient to vaporise the $C_{12}/C_{14}$ portion of the stream but not the $C_{16}/C_{18}$ portion of the stream. It is a matter of routine for the skilled man to assess the amount of hydrogen required to achieve this. The hydrogen stream which now also comprises the vaporised $C_{12}/C_{14}$ is passed in line 4 to the first reaction zone 5 where it is subjected to hydrogenation. The product stream is passed in line 6 to a first separator 7. The desired $C_{12}/C_{14}$ is recovered in line 8 and the lower alkyl alcohol is removed in line 9. The hydrogen is recovered in line 10.

The recovered hydrogen in line 10 is then passed to the second vaporisation zone 11 where in combination with additional hydrogen added in line 13 it contacts the $C_{16}/C_{18}$ portion of the feed which has been passed from the first vaporisation zone 2 to the second vaporisation zone 11 in line 12. The total amount of hydrogen, comprising the recovered hydrogen supplied in line 10 and additional hydrogen supplied in line 13, will be sufficient to vaporise the $C_{16}/C_{18}$ portion of the feed. It is a matter of routine for the skilled man to assess the amount of hydrogen required to achieve this. The hydrogen stream which now also comprises the vaporised $C_6/C_{18}$ is passed in line 14 to the second reaction zone 15 where it is subjected to hydrogenation. The product stream is passed in line 16 to a second separator 17. The desired $C_{16}/C_{18}$ is recovered in line 18 and the lower alkyl alcohol is removed in line 19. The hydrogen is recovered from the second separator 17 and returned in line 20 where it may replace or be added to the hydrogen fed to the first vaporisation zone 2 for further reaction.

Figure 2:
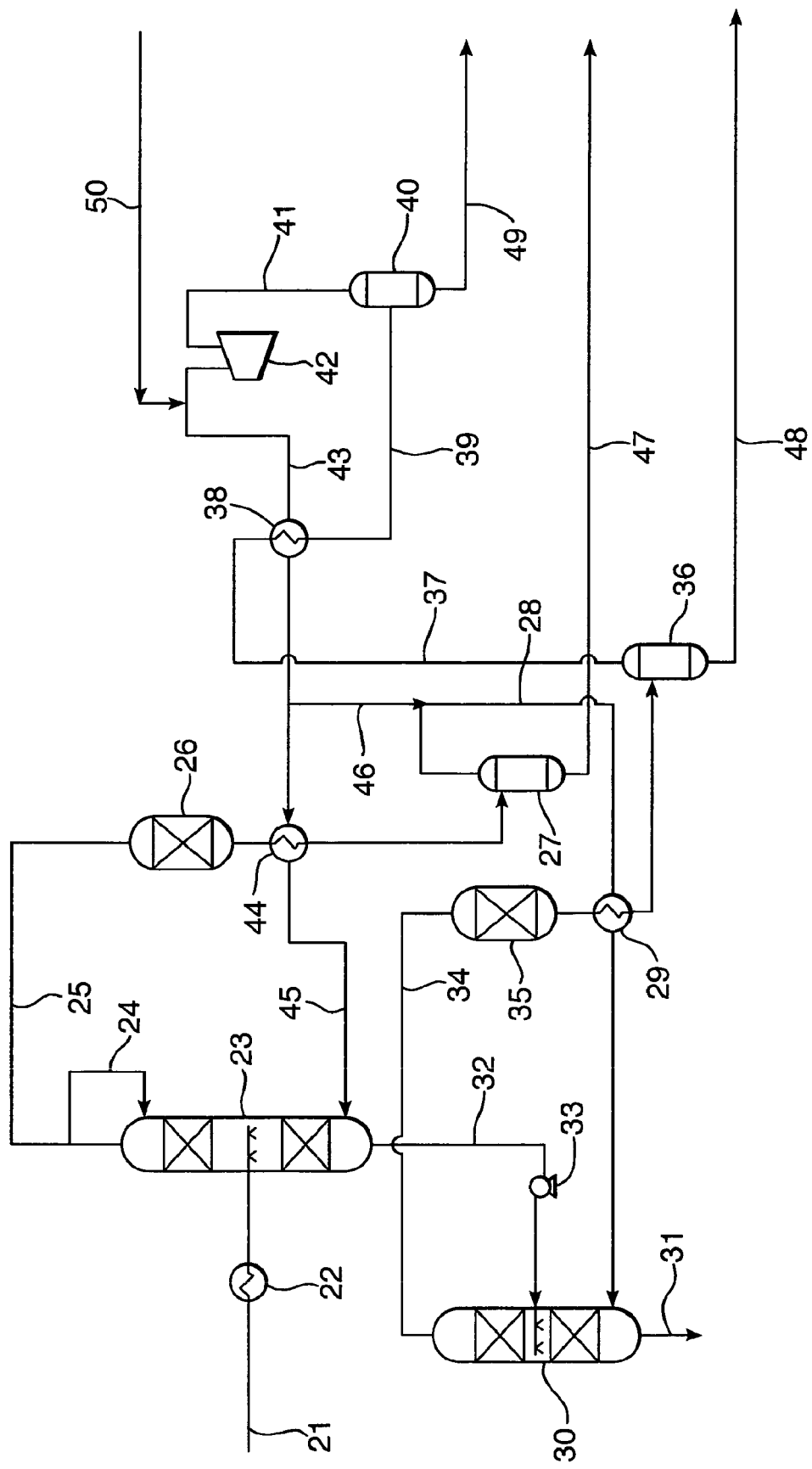
FIG. 2 is a schematic representation of one embodiment of the present invention.

A preferred and more detailed embodiment of the present invention is illustrated in FIG. 2. Again the feed stream comprises a lower alkyl ester, preferably a lower methyl ester, of $C_{12}/C_{14}/C_{16}/C_{18}$ carboxylic acids. The esters may have been formed by any suitable means. Examples of a suitable esterification process is described in EP0454719 which is incorporated herein by reference. The first vaporisation zone 23 is provided with hydrogen in line 45. Fresh hydrogen is provided to the system in line 50. It is mixed with recycled hydrogen recovered from the third separator 40 after compressor 42. The combined stream of new and recycled hydrogen stream is then supplied in line 43 to heat exchanger 38. The warmed hydrogen stream is then split with the amount of hydrogen required for the first vaporisation zone 23 being further heated in heat exchanger 44 before being supplied in line 45 to the first vaporisation zone 23. The amount of hydrogen provided will be sufficient to vaporise the $C_{12}/C_{14}$ portion of the stream but not the $C_{16}/C_{18}$ portion of the stream. It is a matter of routine for the skilled man to assess the amount of hydrogen required to achieve this.

The feed stream of lower alkyl ester, preferably a lower methyl ester, of $C_{12}/C_{14}/C_{16}/C_{18}$ carboxylic acids is fed to the first vaporisation zone 23 in line 21 having been first subjected to pre-heating in heat exchanger 22. The lower alkyl ester, preferably a lower methyl ester, of $C_{12}/C_{14}$ carboxylic acids is then vaporised and removed in line 25. A reflux loop 24 may be provided to aid separation.

The hydrogen stream which now also comprises the vaporised $C_{12}/C_{14}$ is passed in line 25 to the first reaction zone 26 where it is subjected to hydrogenation in the presence of a suitable catalyst. The product stream is passed in first separator 27 via heat exchanger 44 where it is cooled in countercurrent heat exchange to the hydrogen stream 44.

The desired product is separated in first separator 27 and then removed in line 47. The hydrogen is removed from the top of the first separator 27 and, having been combined with additional hydrogen supplied in line 46, is heated in heat exchanger 29 before being passed to the second vaporiser 30.

The unvaporised ester of the $C_{16}/C_{18}$ carboxylic acid, is removed from the first vaporiser 23 and then pumped using pump 33 to the first vaporiser where it is vaporised by and into the hydrogen. Any heavies are removed in line 31.

The hydrogen stream comprising the vaporised $C_{16}/C_{18}$ carboxylic acid will be removed as overhead from the second vaporiser 30 in line 34 and then passed to the second reactor 35 where it is subjected to hydrogenation in the presence of a suitable catalyst. The product stream is removed and then cooled in heat exchanger 29 against the hydrogen stream to the second vaporiser before being passed to the second separator 36. The desired product is then removed from the separator in line 48. The hydrogen is removed in line 37, cooled in heat exchanger 38 and then passed in line 39 to a third separator 40. The lower alcohol produced by the hydrogenation reaction of the lower alkyl ester is removed in line 49.

The hydrogen is then removed in line 41 and passed through compressor 42 before being recycled to the system.

EXAMPLES

The aim of the experiment was to split the feed so that the methyl esters of $C_{12}/C_{14}$ fatty acids were taken overhead and the methy esters of $C_{16}/C_{18}$ fatty acids were removed from the vaporiser as liquid, with the cut being as clean as possible.

The catalyst temperatures in reactor 26 were 218° C. at start up and increased to 235° C. at the end of life. The catalyst in reactor 35 would be at 225° C. to 235° C., each reactor had different catalyst volume contained therein. Less catalyst was required in reactor 35 as higher temperatures of reaction are used and the reaction rate of the higher carbon compounds was noted. This enables high conversions and good selectiveness to be achieved with both the split feed streams over the hydrogenation catalysts. The feed composition is set out in Table 1 and the operating conditions are in Table 2.

TABLE 1

| Fatty Acid Ester | Feed wt % |
|---|---|
| C10 and below | 0.5 |
| C12 | 50.7 |
| C14 | 16.6 |
| C16 | 9.2 |
| C18:0 | 2.6 |
| C18:1 | 16.8 |
| C18:2 | 3.3 |
| Higher | 0.3 |

TABLE 2

| Example No | Feed Rate (g/hr) | Rx Press (psig) | Vap Bot (° C.) | Vap Exit (° C.) | $H_2$ Recycle Flow (h/hr) |
|---|---|---|---|---|---|
| 1 | 250 | 574 | 254 | 225 | 300 |
| 2 | 250 | 572 | 251 | 125 | 400 |
| 3 | 250 | 565 | 260 | 192 | 475 |
| 4 | 250 | 565 | 263 | 217 | 450 |
| 5 | 250 | 565 | 271 | 156 | 450 |
| 6 | 250 | 565 | 275 | 167 | 449 |
| 7 | 250 | 565 | 277 | 181 | 450 |
| 8 | 250 | 565 | 277 | 181 | 551 |

The vaporiser exit sample was condensed, without contacting the hydrogenation catalyst, to allow ease of analysis and mass balance purposes, i.e. no weight change due to reaction. The feed had approximately 30% methanol added to allow the feed to be readily pumped into the system. The results are set out in Table 3.

TABLE 3

Weight Percent Product Analysis (on methanol free basis)

| Example | | grams | C10 | C12 | C14 | C16 | C18 |
|---|---|---|---|---|---|---|---|
| 1 | Btm wt | 26 | 0.68 | 1.51 | 5.54 | 24.84 | 67.43 |
| | Ohs wt | 132 | 0.42 | 71.02 | 19.08 | 6.77 | 2.71 |
| 2 | Btm wt | 137 | 0.17 | 56.16 | 20.07 | 14.81 | 8.79 |
| | Ohs wt | 246 | 1.84 | 90.58 | 6.38 | 0.96 | 0.24 |
| 3 | Btm wt | 113 | 0.09 | 1.04 | 10.81 | 32.20 | 55.86 |
| | Ohs wt | 309 | 0.71 | 79.08 | 19.66 | 0.14 | 0.41 |
| 4 | Btm wt | 29 | 0.24 | 0.71 | 5.32 | 20.49 | 73.25 |
| | Ohs wt | 634 | 0.58 | 57.39 | 19.49 | 11.53 | 11.01 |
| 5 | Btm wt | 109 | 0.06 | 29.08 | 24.23 | 17.97 | 28.65 |
| | Ohs wt | 235 | 0.84 | 96.93 | 0.67 | 0.64 | 0.91 |
| 6 | Btm wt | 65.6 | 0.04 | 4.95 | 28.32 | 25.53 | 41.17 |
| | Ohs wt | 196.1 | 0.54 | 97.54 | 0.96 | 0.28 | 0.67 |
| 7 | Btm wt | 57.9 | 0.04 | 0.21 | 0.91 | 31.34 | 67.50 |
| | Ohs wt | 329.3 | 0.44 | 77.44 | 20.19 | 1.74 | 0.19 |
| 8 | Btm wt | 36.5 | 0.04 | 0.18 | 0.84 | 31.75 | 67.19 |
| | Ohs wt | 171.6 | 0.44 | 76.69 | 20.39 | 2.20 | 0.29 |

Examples 7 and 8 gave the optimum separation. Example 1 indicates the difficulty of separation.

The invention claimed is:

1. A process for the co-production of a stream of a fatty alcohol having first carbon chain lengths and a stream of a fatty alcohol having a second carbon chain lengths, said second carbon chain lengths being longer than said first carbon chain lengths, said process comprising the steps of:

(a) supplying a stream comprising lower alkyl esters of fatty acids having chain lengths comprising the first and second chain lengths to a first vaporisation zone and contacting said stream with an amount of hydrogen which is sufficient to vaporise the lower alkyl esters of the fatty acids having the first carbon chain lengths into the hydrogen;

(b) supplying the hydrogen and the vaporised lower alkyl esters of fatty acids having the first carbon chain lengths to a first reaction zone comprising catalyst and operating under reaction conditions to allow hydrogenation to the desired alcohol having first carbon chain lengths;

(c) recovering from the first reaction zone an alcohol product stream having first carbon chain lengths and hydrogen;

(d) separating the stream of fatty alcohol having the first carbon chain lengths from hydrogen;

(e) supplying the unvaporised lower alkyl esters of the fatty acids having second carbon chain lengths remaining from step (a) to a second vaporisation zone;

(f) contacting the unvaporised lower alkyl esters having second carbon chain lengths in the second vaporisation zone with hydrogen recovered in step (d) and an additional amount of hydrogen such that the total amount of hydrogen is sufficient to vaporise the lower alkyl esters having fatty acids of the second carbon chain lengths into the hydrogen;

(g) supplying the hydrogen and the vaporised lower alkyl esters of fatty acids having second carbon chain lengths to a second reaction zone comprising catalyst and operating under reaction conditions to allow hydrogenation to the desired alcohol having second carbon chain lengths; and (h) recovering from the second reaction zone an alcohol product stream having second carbon chain lengths and hydrogen.

2. A process for the co-production of a stream of a $C_{12}/C_{14}$ fatty alcohol and a stream of a $C_{16}/C_{18}$ fatty alcohol comprising the steps of:

(a) supplying a stream comprising lower alkyl esters of $C_{12}/C_{18}$ fatty acids to a first vaporisation zone and contacting said stream with an amount of hydrogen which is sufficient to vaporise the lower alkyl esters of $C_{12}/C_{14}$ fatty acids into the hydrogen;

(b) supplying the hydrogen and the vaporised lower alkyl esters of $C_{12}/C_{14}$ fatty acids to a first reaction zone comprising catalyst and operating under reaction conditions to allow hydrogenation to the desired $C_{12}/C_{14}$ fatty alcohol;

(c) recovering from the first reaction zone a $C_{12}/C_{14}$ fatty alcohol product stream and hydrogen;

(d) separating the stream of $C_{12}/C_{14}$ fatty alcohol from hydrogen;

(e) supplying the unvaporised lower alkyl esters of $C_{16}/C_{18}$ fatty acids remaining from step (a) to a second vaporisation zone;

(f) contacting the unvaporised lower alkyl esters of $C_{16}/C_{18}$ fatty acids in the second vaporisation zone with hydrogen separated in step (d) and an additional amount of hydrogen such that the total amount of hydrogen is sufficient to vaporise the lower alkyl esters of $C_{16}/C_{18}$ fatty acids into the hydrogen;

(g) supplying the hydrogen and the vaporised lower alkyl esters of $C_{16}/C_{18}$ fatty acids to a second reaction zone comprising catalyst and operating under reaction conditions to allow hydrogenation to the desired $C_{16}/C_{18}$ fatty alcohol; and (h) recovering from the second reaction zone a $C_{16}/C_{18}$ fatty alcohol product stream and hydrogen.

3. A process according to claim 2 wherein the amount of hydrogen provided to the first vaporisation zone is a stoichiometric amount required for the amount of lower alkyl esters of the $C_{12}/C_{14}$ fatty acids supplied to the first vaporisation zone.

4. A process according to claim 2 wherein the hydrogen separated in step (d) is combined with the additional hydrogen in the second vaporisation zone.

5. A process according to claim 2 wherein the hydrogen separated in step (d) is combined with the additional hydrogen prior to the second vaporisation zone such that a single hydrogen stream is supplied to the second vaporisation zone.

6. A process according to claim 2 wherein the amount of hydrogen provided may be the stoichiometric amount required for the amount of lower alkyl esters of the $C_{16}/C_{18}$ fatty acids supplied to the second vaporisation zone.

7. A process according to claim 1 wherein the hydrogen recovered in step (h) is recycled for use in the process.

8. A process according to claim 7 wherein make-up hydrogen is added as required to maintain the total amount of hydrogen in the system.

9. A process according to claim 8 wherein a purge is taken to prevent the build-up of undesirable material in the system.

10. A process according to claim 1 wherein the first and second vaporisation zones are separate zones in the same vaporiser.

11. A process according to claim 1 wherein the first and second vaporisation zones are separate vaporisers.

12. A process according to claim 1 wherein the first and second reaction zones are separate zones in the same reactor.

13. A process according to claim 1 wherein the first and second reaction zones are in separate reactors.

* * * * *